(12) United States Patent
Hoss (10) Patent No.: US 12,080,407 B2
(45) Date of Patent: Sep. 3, 2024

(54) METHOD AND SYSTEM FOR PERFORMING DE-IDENTIFIED LOCATION ANALYTICS

(71) Applicant: KONINKLIJKE PHILIPS N.V., Eindhoven (NL)

(72) Inventor: Andrew G. Hoss, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 382 days.

(21) Appl. No.: 17/638,231

(22) PCT Filed: Aug. 21, 2020

(86) PCT No.: PCT/EP2020/073496
§ 371 (c)(1),
(2) Date: Feb. 25, 2022

(87) PCT Pub. No.: WO2021/037720
PCT Pub. Date: Mar. 4, 2021

(65) Prior Publication Data
US 2022/0328171 A1  Oct. 13, 2022

Related U.S. Application Data

(60) Provisional application No. 62/892,614, filed on Aug. 28, 2019.

(51) Int. Cl.
*G06V 20/00* (2022.01)
*G06T 11/00* (2006.01)
(Continued)

(52) U.S. Cl.
CPC .............. *G16H 40/20* (2018.01); *G06T 11/00* (2013.01); *G06V 20/70* (2022.01); *G06V 30/422* (2022.01); *G16H 50/80* (2018.01)

(58) Field of Classification Search
CPC ........ G16H 40/20; G16H 50/80; G06T 11/00; G06V 20/70; G06V 30/422
See application file for complete search history.

(56) References Cited

U.S. PATENT DOCUMENTS

| 2006/0004605 A1* | 1/2006 | Donoghue | G06Q 10/10 705/2 |
| 2007/0094046 A1* | 4/2007 | Cobbs | G16H 10/60 705/2 |

(Continued)

OTHER PUBLICATIONS

International Search Report for PCT/EP2020/073496 filed Aug. 21, 2020.

*Primary Examiner* — Ping Y Hsieh (57) ABSTRACT

A method for performing de-identified location analytics is provided. The method may include generating a de-identified image by removing the identifiable characteristics from a building arrangement image; generating a binary threshold image by processing the de-identified image using a threshold process; generating a segmentation image by removing any segmentation objects of the binary threshold image with an area less than a defined pixel area; extracting room definitions from the segmentation image, wherein each room definition comprises a series of pixels corresponding to an outline of one of the rooms of the building arrangement image; generating a pixilation table, the pixilation table comprising room definition entries corresponding to the room definitions of the segmentation image, wherein each pixel of the segmentation image is mapped to the room definition entry corresponding to the room definition of the outline surrounding the pixel; and assigning a label to each room definition entry.

15 Claims, 6 Drawing Sheets

(51) Int. Cl.
 *G06V 20/70* (2022.01)
 *G06V 30/422* (2022.01)
 *G16H 40/20* (2018.01)
 *G16H 50/80* (2018.01)

(56) References Cited

U.S. PATENT DOCUMENTS

2018/0032645 A1* 2/2018 Wright .................... G06F 30/13
2019/0072395 A1* 3/2019 Namboodiri ............ G06F 30/18

* cited by examiner

METHOD AND SYSTEM FOR PERFORMING DE-IDENTIFIED LOCATION ANALYTICS

CROSS-REFERENCE TO PRIOR APPLICATIONS

This application claims the priority benefit under 35 U.S.C. § 371 of International Patent Application No. PCT/EP2020/073496, filed on Aug. 21, 2020, which claims the priority benefit of U.S. Patent Application No. 62/892,614, filed on Aug. 28, 2019, the contents of which are herein incorporated by reference.

FIELD OF THE DISCLOSURE

The present disclosure is directed generally to methods and systems for performing de-identified location analytics.

BACKGROUND

Detailed patient location and room occupancy information (often referred to as "room traces" or "patient traces") is vital for surveillance and monitoring, identification of clusters and sources of infections, and mitigating and corrective actions for hospital pathogens.

For hospital epidemiology, tracking patient locations over time is essential in understanding the potential route of transmission of an infection or outbreak during a given timeframe. Most infection control practitioners operate within a "care space" which makes unit-specific or location views appealing for performing these activities. However, to perform such investigations, records must be directly accessed and manually matched. Patient location matching is performed manually by infection control specialists, which is time-consuming (due to document matching), tedious (due to electronic health record sifting), and costly (due to high wages). For patient privacy reasons, hospital locations must be de-identified and encrypted when engaging external services.

During a medical encounter, patient locations are recorded and linked via a unique patient medical record number (MRN) within an electronic health record. Patients receiving in-patient care are moved based on their care needs (for example, from the emergency room to computer tomography exam area to operating room to surgical intensive care unit), and each event is recorded with details on the facility, unit, room, bed, etc. Often, this data is highly complex and must be handled as identifiable protected health information. Currently, patient location data (paired with patient infections and related care) is exceedingly challenging to obtain, record, and trace over time. Furthermore, patient room locations and time spent at specific location(s) are treated as protected health information, and given data size and scale, data analysis performed off-site must be performed in a de-identified state.

Some clinical interoperable systems exist in the healthcare domain, but due to data complexity, few are designed to perform patient data transmission based on room or patient traces, and none are well equipped for graphical-based investigations. Moreover, mapping room coordinates (using X, Y, Z axes) via floor plans would be manual, time consuming, and Cartesian coordinates when plotted, could be re-identified. Additionally, once performed, given hospital units are often reconfigured in clinical practice, and room definitions themselves may difficult to define or reconfigure based on usage.

SUMMARY OF THE DISCLOSURE

The present disclosure is directed inventive to methods and systems for performing de-identified location analytics, for example, by removing all identifiable data characteristics (such as coordinates) for off-site data transfer, with location re-identification through use of a look-up table stored on the premises of the hospital. Various embodiments herein are directed to systems and methods allowing a user to view patient data with floor plan overlay. Broadly, the system may receive a building arrangement image (such as a floor plan) from a user or other source (such as a stored database). The system may remove identifiable information from the digital floor plan and generates a table with room definition labels for each pixel in each room. The digital floor plan and table may be stored on the premises of the hospital. Such a system allows for automatic and standardized location extraction, enables hospital or ward views for epidemiological analysis, and allows for easier mapping of locations to salient features (such as endoscopy room, operating room, etc.).

Generally, in one aspect, a computer-based method for performing de-identified location analytics is provided. The method may include the step of receiving a building arrangement image. The building arrangement image may have one or more rooms. The building arrangement image may have one or more identifiable characteristics. The identifiable characteristics may be one or more text objects, one or more colors and/or one or more legends.

The method may further include generating a de-identified image by removing the identifiable characteristics from the building arrangement image.

The method may further include generating a binary threshold image by processing the de-identified image using a threshold process. The binary threshold image may include one or more segmentation objects. The threshold process may be a histogram-based process. The threshold process may be an entropy-based process.

The method may further include generating a segmentation image by removing any segmentation objects with an area less than a defined pixel area from the binary threshold image The method may further include extracting a set of room definitions from the segmentation image via region of interest processing. Each room definition may include a series of pixels corresponding to an outline of one of the rooms of the building arrangement image.

The method may further include generating a pixilation table. The pixilation table may include one or more room definition entries corresponding to the room definitions of the segmentation image. Each pixel of the segmentation image may be mapped to the room definition entry corresponding to the room definition of the outline surrounding the pixel in the segmentation image.

The method may further include assigning a label to each room definition entry of the pixilation table.

According to an example, the method may further include the step of storing the text objects of the building arrangement image in a text image layer.

According to an example, the method may further include the step of mapping the text image layer onto the segmentation image.

According to an example, the method may further include the step of designating one or more regions of the binary threshold image as grey regions. Any pixels within the grey regions may be excluded from further processing.

According to an example, the method may further include the step of mapping a numeric or categorical value onto each label. The labels may be assigned automatically. The labels may be assigned by a user.

Generally, in another aspect, a system for performing de-identified location analytics is provided. The system may include a building arrangement image, wherein the building arrangement image has one or more rooms and one or more identifiable characteristics. The identifiable characteristics may be one or more text objects, one or more colors and/or one or more legends.

The system may further include a processor configured to generate a de-identified image by removing the identifiable characteristics from the building arrangement image.

The processor may be further configured to generate a binary threshold image by processing the de-identified image using a threshold process. The binary threshold image may include one or more segmentation objects.

The processor may be further configured to generate a segmentation image by removing any segmentation objects of the binary threshold image with an area less than a defined pixel area.

The processor may be further configured to extract a set of room definitions from the segmentation image via region of interest processing. Each room definition may include a series of pixels corresponding to an outline of one of the rooms of the building arrangement image.

The processor may be further configured to generate a pixilation table. The pixilation table may include one or more room definition entries corresponding to the room definitions of the segmentation image. Each pixel of the segmentation image may be mapped to the room definition entry corresponding to the room definition of the outline surrounding the pixel in the segmentation image The processor may be further configured to assign a label to each room definition entry of the pixilation table.

According to an example, the processor may be further configured to store the text objects of the building arrangement image in a text image layer.

According to an example, the processor may be further configured to map the text image layer onto the segmentation image.

According to an example, the processor may be further configured to designate one or more regions of the binary threshold image as grey regions. Any pixels within the grey regions may be excluded from further processing.

According to an example, the processor may be further configured to map a numeric or categorical value onto each label. The labels may be assigned automatically. The labels may be assigned by a user.

In various implementations, a processor or controller may be associated with one or more storage media (generically referred to herein as "memory," e.g., volatile and non-volatile computer memory such as RAM, PROM, EPROM, and EEPROM, floppy disks, compact disks, optical disks, magnetic tape, etc.). In some implementations, the storage media may be encoded with one or more programs that, when executed on one or more processors and/or controllers, perform at least some of the functions discussed herein. Various storage media may be fixed within a processor or controller or may be transportable, such that the one or more programs stored thereon can be loaded into a processor or controller so as to implement various aspects as discussed herein. The terms "program" or "computer program" are used herein in a generic sense to refer to any type of computer code (e.g., software or microcode) that can be employed to program one or more processors or controllers.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

These and other aspects of the various embodiments will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the various embodiments.

DETAILED DESCRIPTION OF EMBODIMENTS

The present disclosure describes various embodiments of a system and method for performing de-identified location analytics. More generally, Applicant has recognized and appreciated that it would be beneficial to provide a system configured to remove identifiable information from a floor plan, such as for a hospital, prior to analysis for patient privacy purposes. Applicant has also recognized and appreciated that it would be beneficial to create a table in which the area inside a room of the floor plan may be classified.

Figure 1:
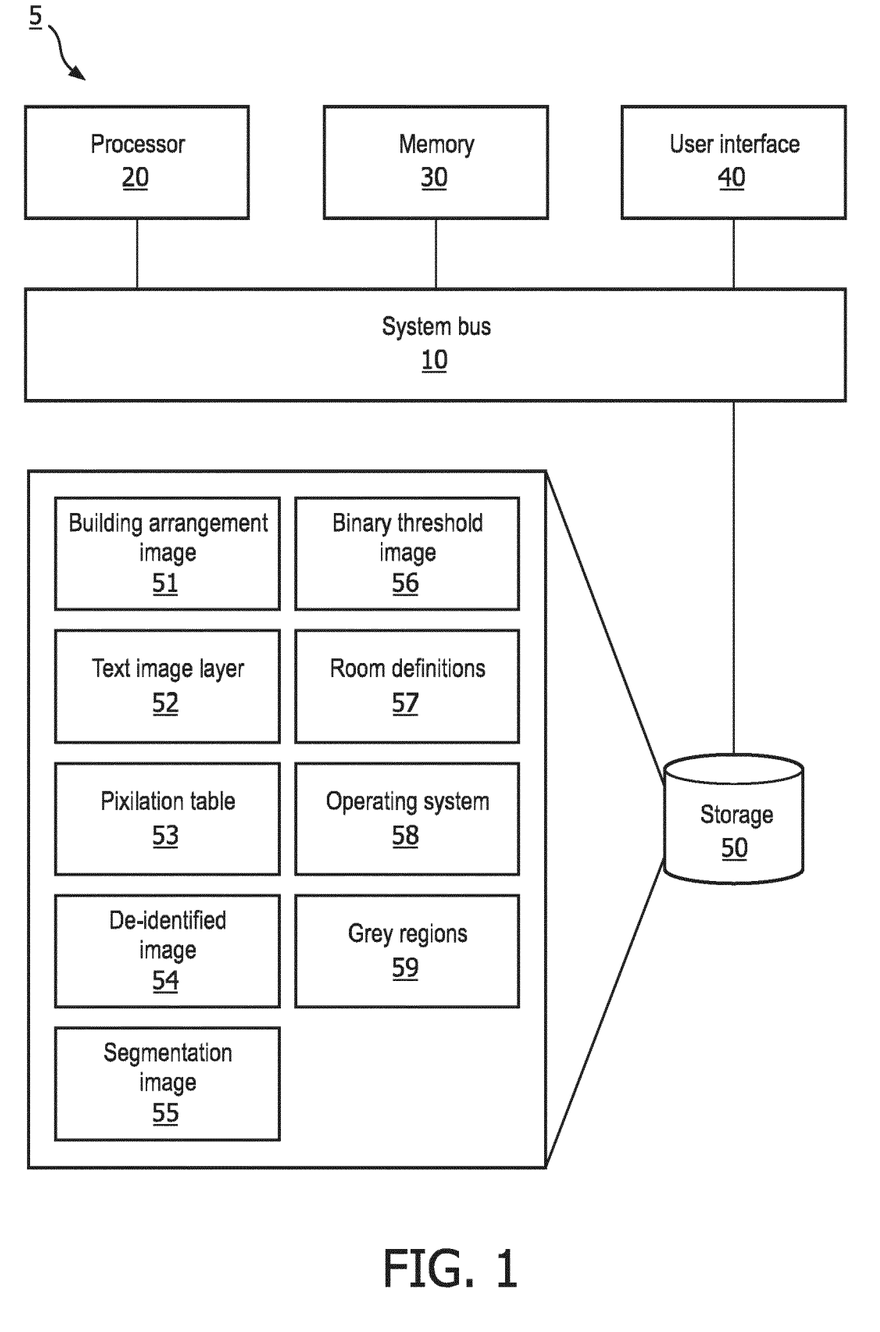
FIG. 1 is a schematic of a system for performing de-identified location analytics, in accordance with an example.

Referring to FIG. 1, in one aspect, a system 5 for performing de-identified location analytics is provided. The system may include a building arrangement image 51, wherein the building arrangement image 51 has one or more rooms and one or more identifiable characteristics. The identifiable characteristics may be one or more text objects, one or more colors, and/or one or more legends. The building arrangement image 51 may be provided by a user via user interface 40. The building arrangement image may also be retrieved from storage 50 or memory 30 via system bus 10.

The system may further include a processor 20 configured to generate a de-identified image 54 by removing the identifiable characteristics from the building arrangement image 51. The de-identified image may be stored in storage 50.

The processor 20 may be further configured to generate a binary threshold image 56 by processing the de-identified image using a threshold process. The binary threshold image 56 may include one or more segmentation objects. The binary threshold image 56 may be stored in storage 50.

The processor 20 may be further configured to generate a segmentation image 55 by removing any segmentation objects of the binary threshold image 56 with an area less than a defined pixel area. The segmentation image 55 may be stored in storage 50.

The processor 20 may be further configured to extract a set of room definitions 57 from the segmentation image 55 via region of interest processing. Each room definition 557 may include a series of pixels corresponding to an outline of one of the rooms of the building arrangement image 51. The room definitions 57 may be stored in storage 50.

The processor 20 may be further configured to generate a pixilation table 53. The pixilation table 53 may include one or more room definition entries corresponding to the room definitions 57 of the segmentation image 55. Each pixel of the segmentation image 55 may be mapped to the room definition entry corresponding to the room definition 557 of the outline surrounding the pixel in the segmentation image 55. The pixilation table may be stored in storage 50.

The processor 20 may be further configured to assign a label to each room definition entry of the pixilation table 53.

According to an example, the processor 20 may be further configured to store the text objects of the building arrangement image 51 in a text image layer 52. The text image layer 52 may be stored in storage 50.

According to an example, the processor 20 may be further configured to map the text image layer 52 onto the segmentation image 55. The text image layer 52 may be stored in storage 50.

Figure 5:
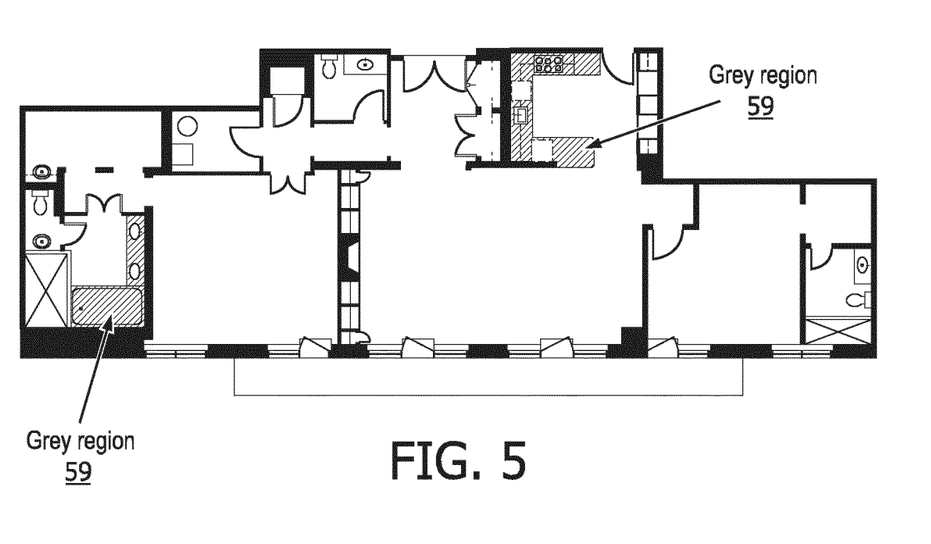
FIG. 5 is a binary threshold with several designated grey regions, in accordance with an example.

According to an example, the processor 20 may be further configured to designate one or more regions of the binary threshold image 56 as grey regions 59. Any pixels within the grey regions may be excluded from further processing 59. FIG. 5 shows an example binary threshold image with designated grey regions 59.

According to an example, the processor 20 may be further configured to map a numeric or categorical value onto each label. The labels may be assigned automatically. The labels may be assigned by a user via a user interface 40.

According to an example, system 5 may include one or more of a processor 20, memory 30, user interface 40, and storage 50, interconnected via one or more system buses 510. It will be understood that FIG. 1 constitutes, in some respects, an abstraction and that the actual organization of the components of the system 5 may be different and more complex than illustrated.

According to an example, system 500 may include a processor 20 capable of executing instructions stored in memory 30 or storage 50 or otherwise processing data to, for example, perform one or more steps of the method. Processor 20 may be formed of one or multiple modules. Processor 20 may take any suitable form, including but not limited to a microprocessor, microcontroller, multiple microcontrollers, circuitry, field programmable gate array (FPGA), application-specific integrated circuit (ASIC), a single processor, or plural processors. Memory 30 can take any suitable form, including a non-volatile memory and/or RAM.

The memory 30 may include various memories such as, for example L1, L2, or L3 cache or system memory. As such, the memory 30 may include static random access memory (SRAM), dynamic RAM (DRAM), flash memory, read only memory (ROM), or other similar memory devices. The memory can store, among other things, an operating system. The RAM is used by the processor for the temporary storage of data. According to an embodiment, an operating system may contain code which, when executed by the processor, controls operation of one or more components of system 5. It will be apparent that, in embodiments where the processor implements one or more of the functions described herein in hardware, the software described as corresponding to such functionality in other embodiments may be omitted.

User interface 40 may include one or more devices for enabling communication with a user. The user interface can be any device or system that allows information to be conveyed and/or received, and may include a display, a mouse, and/or a keyboard for receiving user commands. In some embodiments, user interface 40 may include a command line interface or graphical user interface that may be presented to a remote terminal via communication interface 550. The user interface may be located with one or more other components of the system, or may located remote from the system and in communication via a wired and/or wireless communications network.

Storage 50 may include one or more machine-readable storage media such as read-only memory (ROM), random-access memory (RANI), magnetic disk storage media, optical storage media, flash-memory devices, or similar storage media. In various embodiments, storage 50 may store instructions for execution by processor 20 or data upon which processor 20 may operate. For example, storage 50 may store an operating system 58 for controlling various operations of system 5.

It will be apparent that various information described as stored in storage 50 may be additionally or alternatively stored in memory 30. In this respect, memory 30 may also be considered to constitute a storage device and storage 50 may be considered a memory. Various other arrangements will be apparent. Further, memory 30 and storage 50 may both be considered to be non-transitory machine-readable media. As used herein, the term non-transitory will be understood to exclude transitory signals but to include all forms of storage, including both volatile and non-volatile memories.

While the system 5 for performing de-identified location analytics is shown as including one of each described component, the various components may be duplicated in various embodiments. For example, processor 20 may include multiple microprocessors that are configured to independently execute the methods described herein or are configured to perform steps or subroutines of the methods described herein such that the multiple processors cooperate to achieve the functionality described herein. Further, where one or more components of system 5 is implemented in a cloud computing system, the various hardware components may belong to separate physical systems. For example, processor 20 may include a first processor in a first server and a second processor in a second server. Many other variations and configurations are possible.

Figure 2:
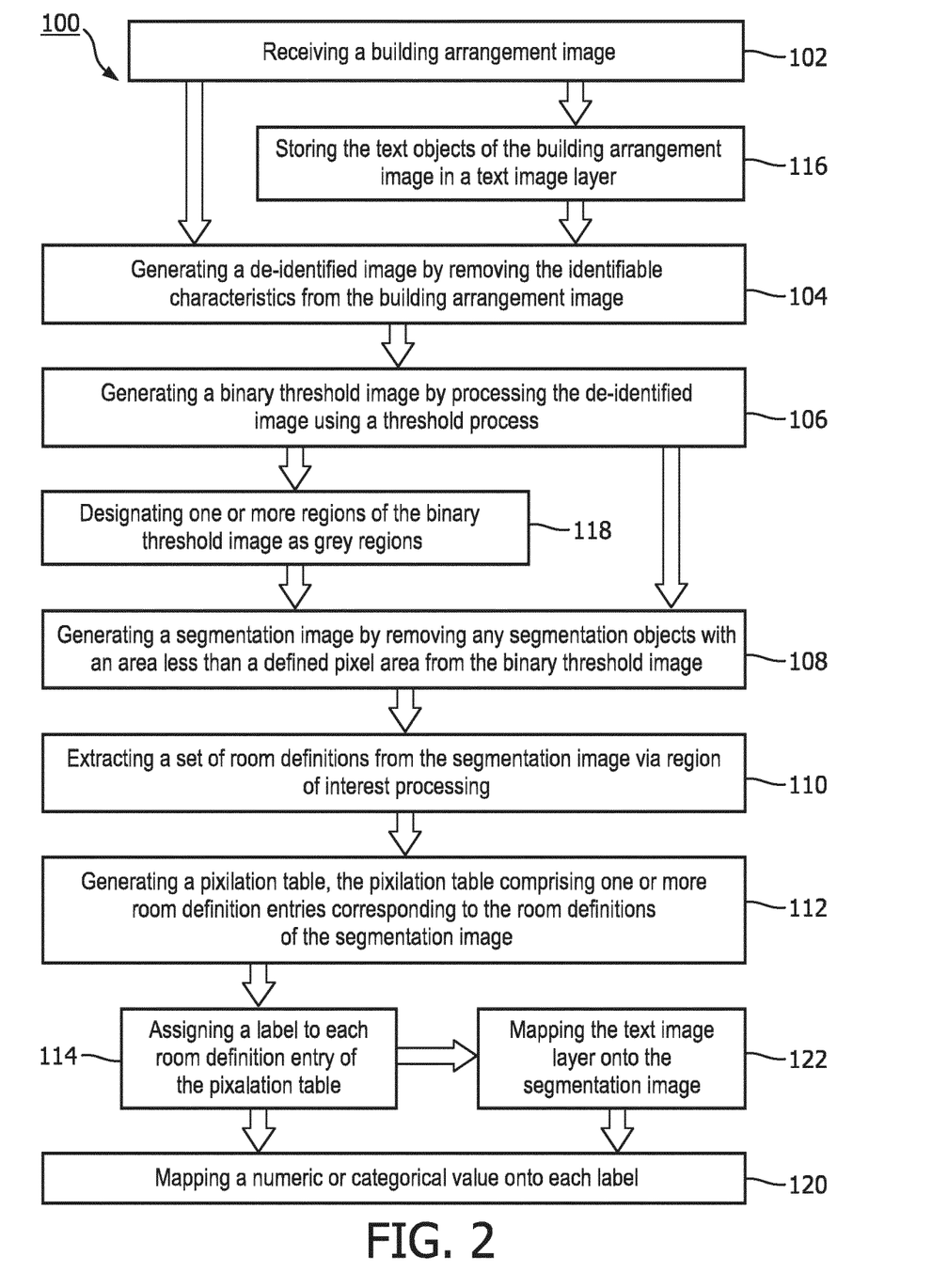
FIG. 2 is a flowchart of a method for performing de-identified location analytics, in accordance with an example.

Referring to FIG. 2, in another aspect, a computer-based method 100 for performing de-identified location analytics is provided.

Figure 3:
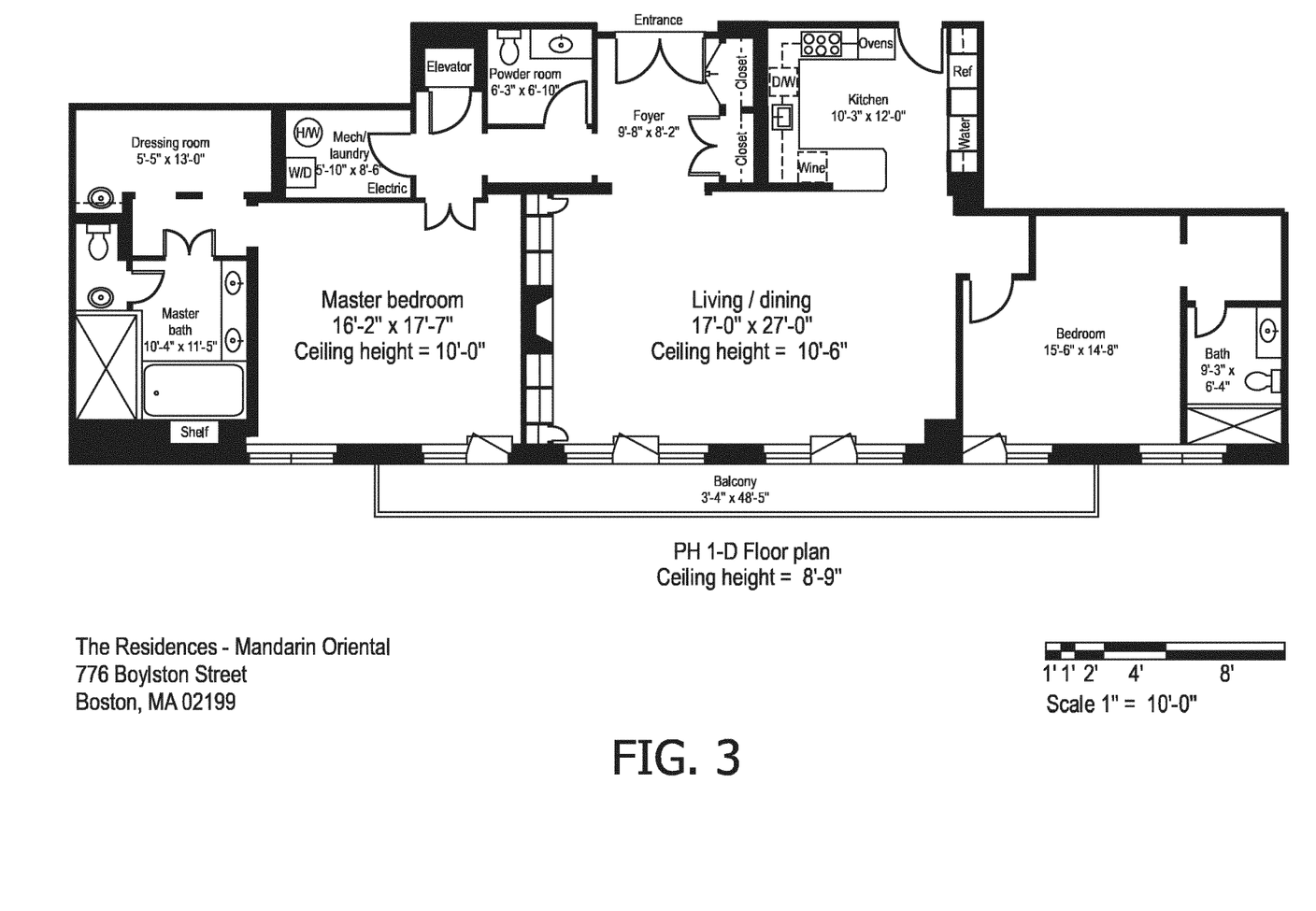
FIG. 3 is an example building arrangement image prior to being processed in accordance with an example.

The method 100 may include the step of receiving 102 a building arrangement image. An example building arrangement image of a residential apartment is shown in FIG. 3. However, the building arrangement image may be of any appropriate building or structure. For example, the building arrangement image may be a floor plan, blueprint, building schematic diagram for a hospital ward.

The building arrangement image may have one or more rooms. As shown in FIG. 3, the example building arrangement image consists of a number of rooms with text labels such as "Master Bedroom", "Master Bath", and "Foyer".

The building arrangement image may have one or more identifiable characteristics. The identifiable characteristics may be one or more text objects, one or more colors, and/or one or more legends. The identifiable characteristics may also be any other feature of the floors plan which could lead a viewer to discern the location. As shown in FIG. 3, the example building arrangement image has a text box stating the name of the apartment building, "The Residences— Mandarin Oriental" and its Boston address. The example building arrangement image also contains a scale in the bottom-right corner.

The method 100 may further include generating 104 a de-identified image by removing the identifiable characteristics from the building arrangement image. This removal may be performed by a software program such as Adobe Illustrator® or any other suitable program. As shown in FIGS. 4-8, the text objects, scale, and other information has been removed. FIGS. 4-8 are described in greater detail below. Further, as described below, the text objects may be saved for further processing.

Figure 4:
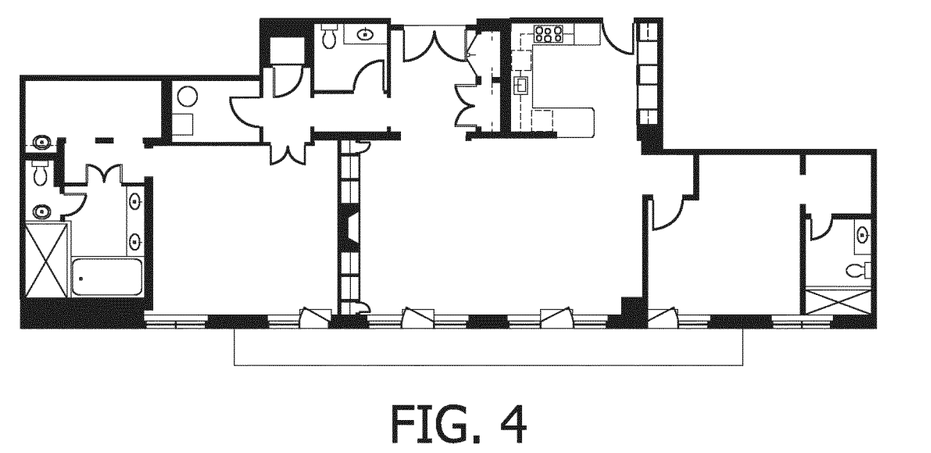
FIG. 4 is a binary threshold image, in accordance with an example.

The method 100 may further include generating 106 a binary threshold image by processing the de-identified image using a threshold process. In an example thresholding regimen, pixels of an image with an intensity above a defined threshold are replaced with black pixels. All other pixels are replaced with white pixels, creating a binary black and white image. FIG. 4 shows an example binary threshold image. The binary threshold image may include one or more segmentation objects.

The threshold process may be a histogram-based process. In a histogram-based threshold process, the threshold levels are set according to a histogram representation of the intensity of the image. The threshold process may be an entropy-based process. In an entropy-based process, the threshold levels are set based on algorithms using the entropy of the foreground and background regions of the image, as well as the cross-entropy between the original and binarized image. The threshold process may be of any other appropriate process. The threshold process may be performed by a software program such as ImageJ.

Figure 6:
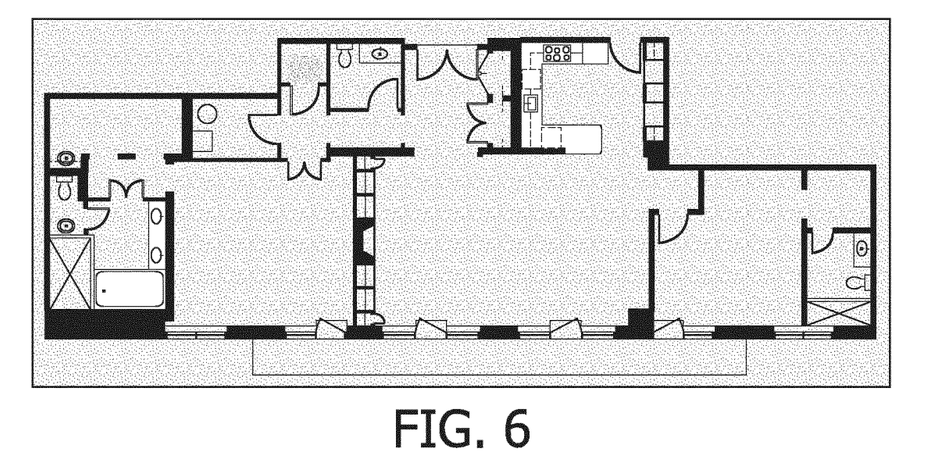
FIG. 6 is a segmentation image, in accordance with an example.

The method 100 may further include generating 108 a segmentation image by removing any segmentation objects with an area less than a defined pixel area from the binary threshold image. An example segmentation image is shown in FIG. 6, where the remaining segmentation objects are outlined in a heavy black line. In this step, software (such as ImageJ) may be used to perform segmentation analysis to define any polygon/object within a defined pixel area range. In one example, watershed separation analysis may be used. The remaining segmentation objects may be considered "room definitions", a term which is expanded upon below.

The method 100 may further include extracting 110 a set of room definitions from the segmentation image via region of interest processing. Each room definition may include a series of pixels corresponding to an outline of one of the rooms of the building arrangement image.

Figure 7:
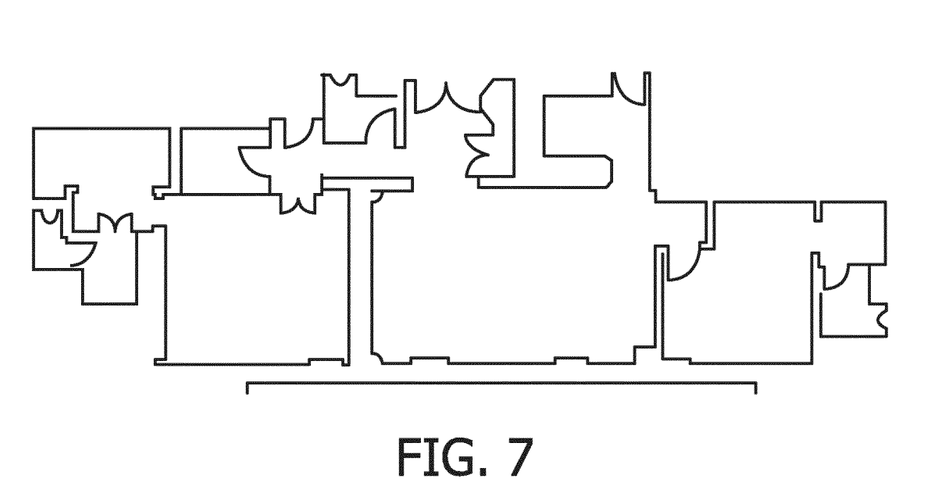
FIG. 7 is a segmentation image with several room definitions, in accordance with an example.

The method 100 may further include generating 112 a pixilation table. The pixilation table may include one or more room definition entries corresponding to the room definitions of the segmentation image. Each pixel of the segmentation image may be mapped to the room definition entry corresponding to the room definition of the outline surrounding the pixel in the segmentation image. Initially, each room definition entry may be assigned a random, unique label, such as "1-i". FIG. 7 shows an example room definition image, where each room definition may be identified with a single colorized pixel within its region of interest.

Figure 8:
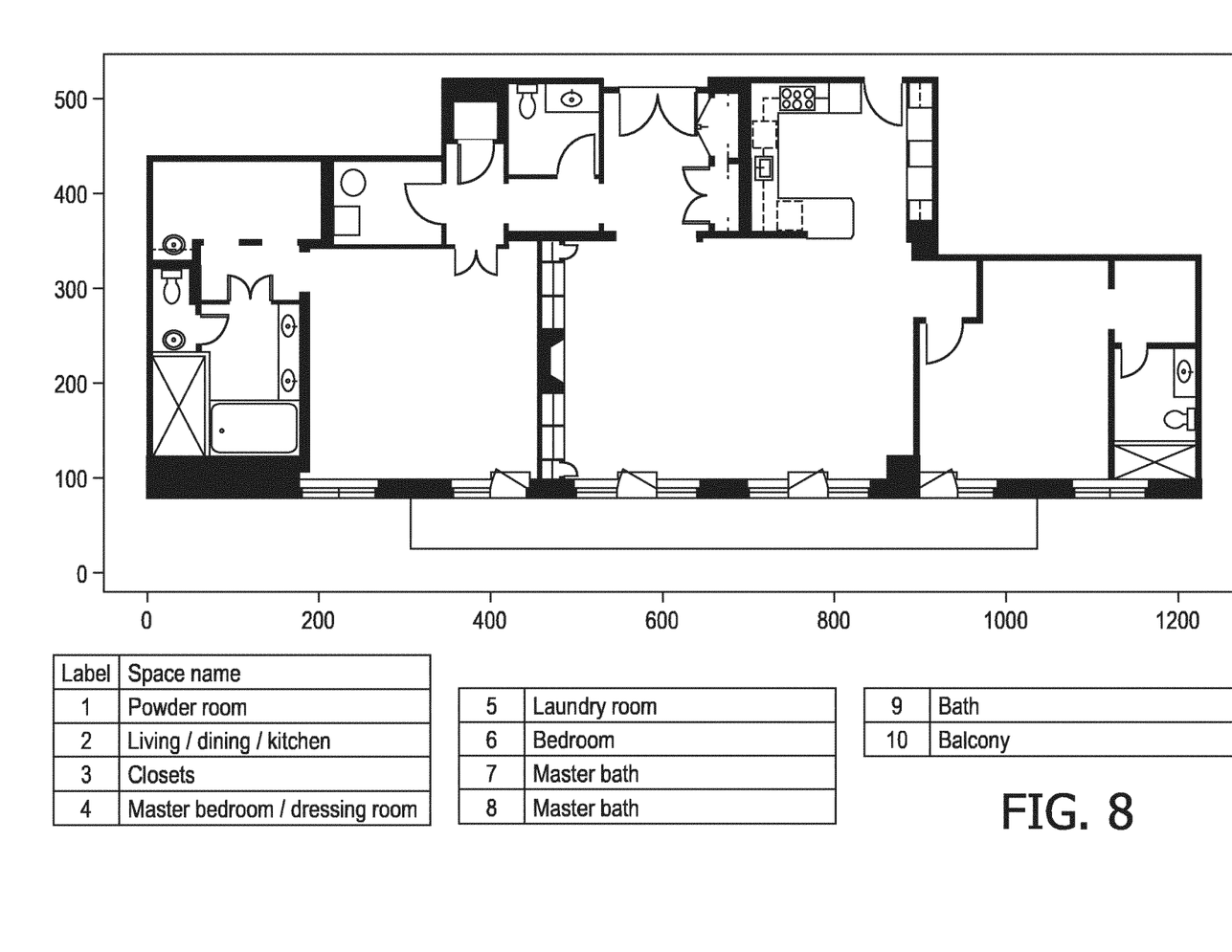
FIG. 8 is a segmentation image and pixilation tables, in accordance with an example.

The method 100 may further include assigning 114 a label to each room definition entry of the pixilation table. FIG. 8 shows an example segmentation image with overlaid labels from the pixilation table. The labels may be assigned automatically by a software program. The labels may be assigned manually by a user via a user interface. In further examples, the color hue and saturation may also be assigned in the pixilation table in a manner similar to the room definition labels.

According to an example, the method 100 may further include the step of storing 116 the text objects of the building arrangement image in a text image layer. In other examples, additional information from the building arrangement image, such as colors or legends, may also be stored. According to an example, the method 100 may further include the step of mapping 122 the text image layer onto the segmentation image. By implementing this step, the initial text shown on the building arrangement image may be reapplied to the processed image for easier visual analysis.

According to an example, the method 100 may further include the step of designating 118 one or more regions of the binary threshold image as grey regions. Any pixels within the grey regions may be excluded from further processing. In the example shown in FIG. 5, the bathroom and kitchen are "greyed" out. In a hospital epidemiology analysis, it may be appropriate to grey out regions where patients are not present, such as administrative or maintenance areas. The grey regions may be designated automatically. The grey regions may be designated manually by a user.

According to an example, the method 100 may further include the step of mapping 120 a numeric or categorical value onto each label. The values may be assigned automatically. The values may be assigned by a user. The values may correspond to measurements relating to infectious diseases or other, related metrics.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. A computer-based method for performing de-identified location analytics, comprising the steps of:
   receiving a building arrangement image, wherein the building arrangement image has one or more rooms and one or more identifiable characteristics;
   generating a de-identified image by removing the identifiable characteristics from the building arrangement image;
   generating a binary threshold image by processing the de-identified image using a threshold process, wherein the binary threshold image comprises one or more segmentation objects;
   generating a segmentation image by removing any segmentation objects with an area less than a defined pixel area from the binary threshold image;
   extracting a set of room definitions from the segmentation image via region of interest processing, wherein each room definition comprises a series of pixels corresponding to an outline of one of the rooms of the building arrangement image;
   generating a pixilation table, the pixilation table comprising one or more room definition entries corresponding to the room definitions of the segmentation image, wherein each pixel of the segmentation image is mapped to the room definition entry corresponding to the room definition of the outline surrounding the pixel in the segmentation image; and
   assigning a label to each room definition entry of the pixilation table.

2. The method of claim 1, wherein the identifiable characteristics are one or more text objects, one or more colors, and/or one or more legends.

3. The method of claim 2, further comprising the step of storing the text objects of the building arrangement image in a text image layer.

4. The method of claim 3, further comprising the step of mapping the text image layer onto the segmentation image.

5. The method of claim 1, further comprising the step of designating one or more regions of the binary threshold image as grey regions, wherein any pixels within the grey regions are excluded from further processing.

6. The method of claim 1, wherein the threshold process is a histogram-based process.

7. The method of claim 1, wherein the threshold process is an entropy-based process.

8. The method of claim 1, further comprising the step of mapping a numeric or categorical value onto each label.

9. The method of claim 1, wherein the labels are assigned automatically.

10. A system for performing de-identified location analytics, comprising:
    a building arrangement image, wherein the building arrangement image has one or more rooms and one or more identifiable characteristics; and
    a processor configured to: (i) generate a de-identified image by removing the identifiable characteristics from the building arrangement image; (ii) generate a binary threshold image by processing the de-identified image using a threshold process, wherein the binary threshold image comprises one or more segmentation objects; (iii) generate a segmentation image by removing any segmentation objects of the binary threshold image with an area less than a defined pixel area; (iv) extract a set of room definitions from the segmentation image via region of interest processing, wherein each room definition comprises a series of pixels corresponding to an outline of one of the rooms of the building arrangement image; (v) generate a pixilation table, the pixilation table comprising one or more room definition entries corresponding to the room definitions of the segmentation image, wherein each pixel of the segmentation image is mapped to the room definition entry corresponding to the room definition of the outline surrounding the pixel in the segmentation image; and (vi) assign a label to each room definition entry of the pixilation table.

11. The system of claim 10, wherein the identifiable characteristics are one or more text objects, one or more colors, and/or one or more legends.

12. The system of claim 11, wherein the processor is further configured to store the text objects of the building arrangement image in a text image layer.

13. The system of claim 12, wherein the processor is further configured to map the text image layer onto the segmentation image.

14. The system of claim 10, wherein the processor is further configured to designate one or more regions of the binary threshold image as grey regions, wherein any pixels within the grey regions are excluded from further processing.

15. The system of claim 10, wherein the processor is further configured to map a numeric or categorical value onto each label.

* * * * *